(12) United States Patent
Blumberg (10) Patent No.: US 10,849,437 B2
(45) Date of Patent: *Dec. 1, 2020

(54) DIGITAL BED SYSTEM

(71) Applicant: Sleep Technologies, LLC, Rio Hondo, TX (US)

(72) Inventor: J. Seth Blumberg, Vail, CO (US)

(73) Assignee: SLEEP TECHNOLOGIES, LLC, Rio Hondo, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/595,151

(22) Filed: Oct. 7, 2019

(65) Prior Publication Data

US 2020/0046136 A1 Feb. 13, 2020

Related U.S. Application Data

(63) Continuation of application No. 15/457,723, filed on Mar. 13, 2017, now Pat. No. 10,433,653, which is a
(Continued)

(51) Int. Cl.
*A47C 27/08* (2006.01)
*A47C 23/00* (2006.01)
*A47C 27/10* (2006.01)
*A61B 5/11* (2006.01)
*A61B 5/00* (2006.01)
*A47C 17/04* (2006.01)
*A47C 17/34* (2006.01)
*A47C 17/62* (2006.01)

(52) U.S. Cl.
CPC ............ *A47C 27/083* (2013.01); *A47C 17/04* (2013.01); *A47C 17/34* (2013.01); *A47C 17/62* (2013.01); *A47C 23/002* (2013.01); *A47C 27/10* (2013.01); *A61B 5/1116* (2013.01); *A61B 5/1126* (2013.01); *A61B 5/6887* (2013.01); *A61B 5/6892* (2013.01); *A61B 5/4504* (2013.01); *A61B 5/4528* (2013.01); *A61B 2562/0247* (2013.01); *A61B 2562/046* (2013.01)

(58) Field of Classification Search
CPC ............ A61G 7/05769; A61G 7/05776; A61G 2203/34; A61G 2200/34; A61G 7/1021
See application file for complete search history.

(56) References Cited

U.S. PATENT DOCUMENTS 4,799,276 A * 1/1989 Kadish ................. A61G 7/0573
137/901
4,864,671 A * 9/1989 Evans ................ A61G 7/05776
5/713

(Continued)

*Primary Examiner* — Eric J Kurilla
(74) *Attorney, Agent, or Firm* — Bell Nunnally & Martin LLP (57) ABSTRACT

In one embodiment, the digital bed system is comprised of an array of support cells. Each support cell is capable of communicating with a controller and increasing and decreasing in firmness in response to commands issued by a controller. The support cells are operatively connected to a communication channel that is also connected to a controller. The controller is capable of receiving data from the support cells and is also capable of issuing commands to each of the support cells. The controller is programmed issue commands to increase or decrease the firmness of individual support cells within the support cells.

13 Claims, 2 Drawing Sheets

Related U.S. Application Data continuation of application No. 11/851,204, filed on Sep. 6, 2007, now Pat. No. 9,591,995.

(60) Provisional application No. 60/842,375, filed on Sep. 6, 2006.

(56) References Cited

U.S. PATENT DOCUMENTS

| | | | | |
|---|---|---|---|---|
| 4,941,478 A * | 7/1990 | Takeuchi | A61F 5/56 | 128/848 |
| 5,103,519 A * | 4/1992 | Hasty | A61G 7/05776 | 5/621 |
| 5,192,304 A * | 3/1993 | Rassman | A61H 9/0078 | 5/933 |
| 5,283,735 A * | 2/1994 | Gross | A47C 4/54 | 600/587 |
| 5,373,595 A * | 12/1994 | Johnson | A61G 7/05769 | 285/361 |
| 5,542,907 A * | 8/1996 | Chou | A61H 23/0263 | 601/46 |
| 5,687,438 A * | 11/1997 | Biggie | A61G 5/1043 | 297/284.6 |
| 5,873,137 A * | 2/1999 | Yavets-Chen | A61G 7/05776 | 5/188 |
| 6,073,291 A * | 6/2000 | Davis | A61B 6/0485 | 414/676 |
| 6,336,235 B1 * | 1/2002 | Ruehl | A61G 7/00 | 297/354.13 |
| 6,351,678 B1 * | 2/2002 | Borders | A61F 7/007 | 700/83 |
| 6,353,950 B1 * | 3/2002 | Bartlett | A61G 7/001 | 5/609 |
| 6,487,739 B1 * | 12/2002 | Harker | A61G 7/05707 | 5/423 |
| 6,684,434 B2 * | 2/2004 | Ellis | A61G 7/05769 | 5/710 |
| 6,829,797 B2 * | 12/2004 | Partian | A61G 7/057 | 5/710 |
| 6,859,967 B2 * | 3/2005 | Harrison | A61G 7/001 | 5/710 |
| 6,915,538 B2 * | 7/2005 | Treon | A61G 13/02 | 318/260 |
| 6,941,598 B2 * | 9/2005 | Ferrand | A61G 7/00 | 5/600 |
| 9,591,995 B2 * | 3/2017 | Blumberg | A47C 23/002 | |
| 10,433,653 B2 * | 10/2019 | Blumberg | A47C 17/62 | |
| 2006/0075559 A1 * | 4/2006 | Skinner | A61G 7/05769 | 5/615 |
| 2006/0085919 A1 * | 4/2006 | Kramer | A47C 27/082 | 5/713 |
| 2007/0239370 A1 * | 10/2007 | Block | A47C 23/125 | 702/41 |
| 2008/0034501 A1 * | 2/2008 | Hyde | A61F 5/05 | 5/613 |

\* cited by examiner

FIG. 1

DIGITAL BED SYSTEM

This application is a continuation of U.S. application Ser. No. 15/457,723 filed Mar. 13, 2017, which is a continuation of U.S. application Ser. No. 11/851,204 filed Sep. 6, 2007, which claims priority from U.S. Provisional Patent Application Ser. No. 60/842,375 entitled "Digital Bed System" filed Sep. 6, 2006, all of which are incorporated herein by reference in their entirety.

This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

FIELD OF THE INVENTION

The present invention relates in general to the field of body support systems for sleep or resting, and in particular body support systems for sleep or resting controlled by a controller.

BACKGROUND OF THE INVENTION

Typically, a conventional bed provides a flat surface of uniform firmness for sleeping. While many sleepers find such an arrangement to be comfortable, enjoyable, and conducive to sleep, other sleepers have special needs or desires. For example, some sleepers may simply prefer to have their feet raised when sleeping or to be able to adjust the firmness of the sleeping surface. Other sleepers with chronic injuries may require special arrangements to relieve pressure on particular body parts or have traction applied to other body parts.

A number of adjustable beds have been brought to market that provide limited solutions. For example, there are beds with adjustable contours. There are also beds which allow the firmness of the sleeping surface to be adjusted. These solutions, however, are limited in application. Adjustments can be slow and cumbersome and may be inadequate if the sleeper changes position. No solution actively monitors the position of the sleeper and dynamically adjusts the sleeping surface in a manner finely tailored to the individual sleeper's needs.

OBJECTS AND SUMMARY OF THE INVENTION

It is therefore an object of this invention to provide a programmable sleep support system that can dynamically adjust to the needs of a variety of users.

In one embodiment, the digital bed system is comprised of an array support cells. Each support cell is capable of communicating with a controller and increasing and decreasing in firmness in response to commands issued by a controller. The support cells are operatively connected to a communication channel that is also connected to a controller. The controller may be an embedded device, controller, controller equipment, or a server, and is capable of receiving data from the support cells and is also capable of issuing commands to each of the support cells. The controller is programmed issue commands to increase or decrease the firmness of individual support cells within the support cells.

BRIEF DESCRIPTION OF THE DRAWINGS

The foregoing and other objects, features, and advantages of the invention will be apparent from the following more particular description of preferred embodiments as illustrated in the accompanying drawings, in which reference characters refer to the same parts throughout the various views. The drawings are not necessarily to scale, emphasis instead being placed upon illustrating principles of the invention.

DETAILED DESCRIPTION OF THE PREFERRED EMBODIMENTS

Reference will now be made in detail to the preferred embodiments of the present invention, examples of which are illustrated in the accompanying drawings.

In one embodiment, the digital bed system is comprised of an array of independently controllable support cells support cells. Each support cell is capable of communicating with a controller and increasing and decreasing in firmness in response to commands issued by a controller. The support cells are operatively connected to a communication channel that is also connected to a controller. The controller is capable of receiving data from the support cells and is also capable of issuing commands to each of the support cells. The controller is programmed issue commands to increase or decrease the firmness of individual support cells within the support cells.

Reference will now be made in detail to embodiments of the present invention, examples of which are illustrated in the accompanying drawings.

Figure 1:
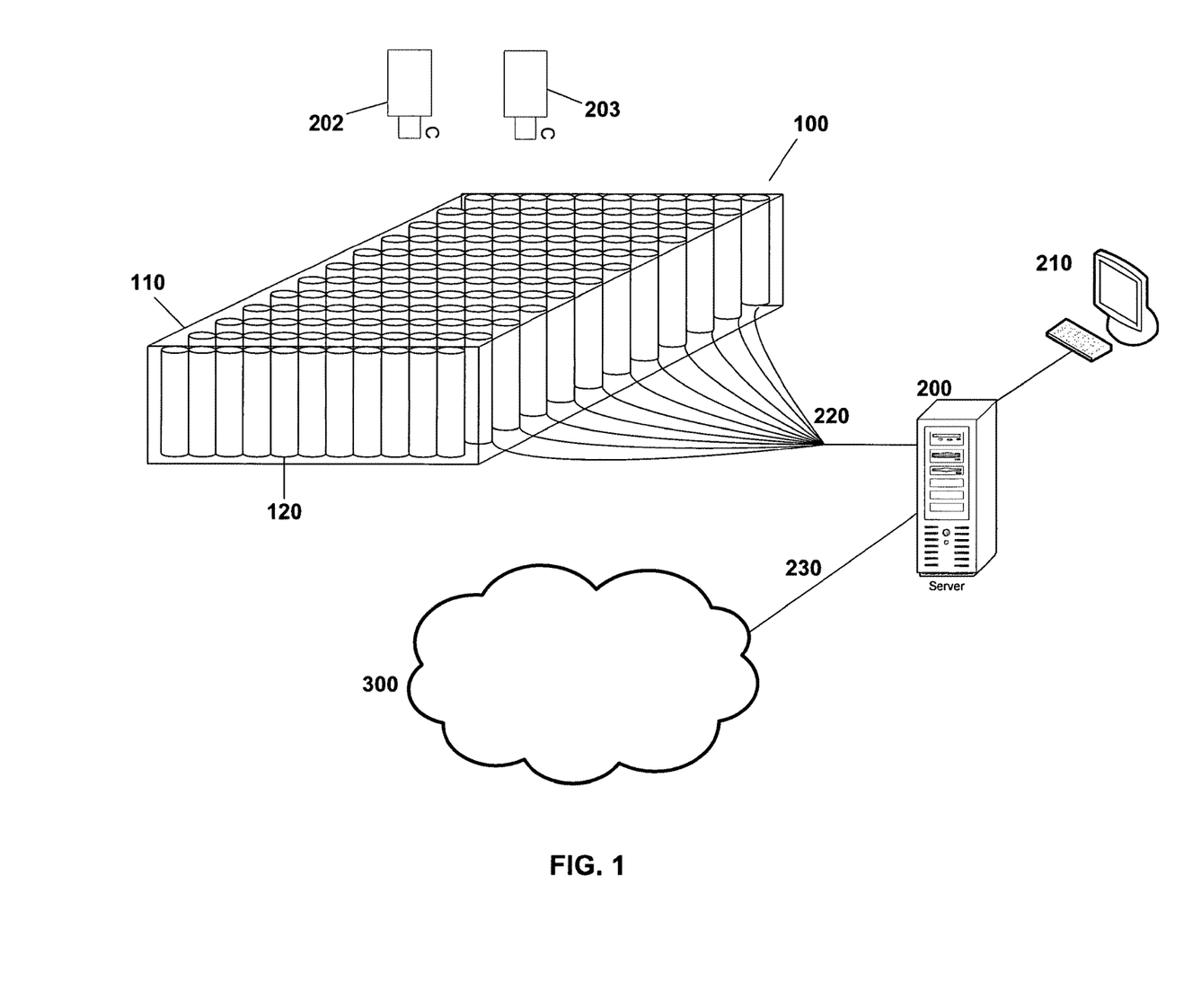
FIG. 1 shows a diagram of one embodiment of the system.

Referring to FIG. 1, an embodiment of the system is comprised of a bed, 100, composed of an array plurality of individual support cells, 120, mounted within a bed frame, 110. The support cells 120 may comprise any suitable actuating means, including, e.g., electromagnetic, hydraulic, electrical, plasma, servo, piston, or screw-type actuators. Each support cell 120 may further comprise any suitable sensor device, including, e.g., one or more mechanical, optical, electrical, pressure, infrared, millimeter wave, sonar, GPS, and temperature sensors, that together can be used to determine, for example, the position of the body or specific body parts.

Figure 2:
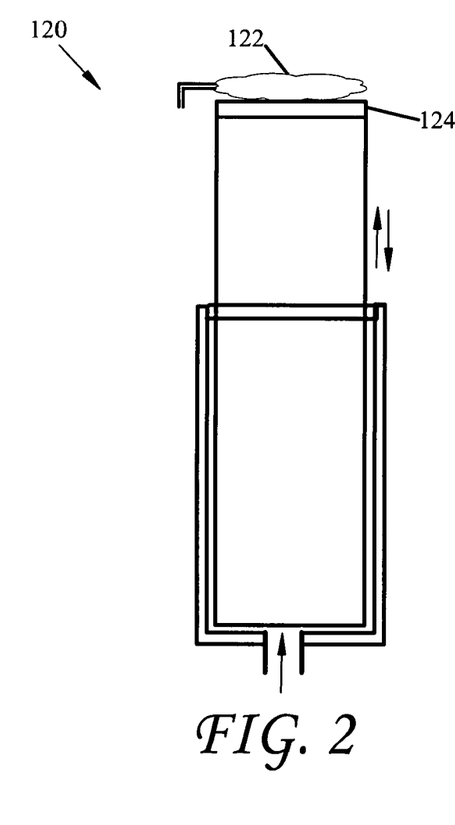
FIG. 2 shows one embodiment of a support cell.
Figure 3:
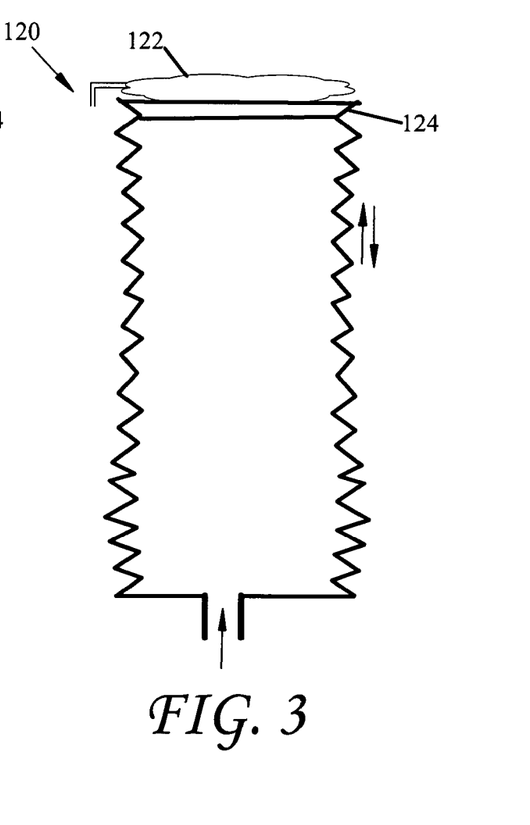
FIG. 3 shows an alternate embodiment of a support cell.

Each of the support cells, 120, may include one or more sensors integrated with the support cell, so as to be capable of measuring resistance, pressure, actuator position, heat, or other measurable state to determine any or all of the following: (a) if any body part, such as the knee, shoulder, elbow, toes, head, or breast, is on that cell; (b) if there is a sharp and/or bony body part, such as an elbow, or toe, on that cell; and/or (c) if there is soft tissue such as the belly, on that part of the bed. Alternatively, multiple cells may share a sensor or sensors. FIGS. 2 and 3 show alternate embodiments of a support cell, 120. FIG. 2 shows a rigid piston-based embodiment, while FIG. 3 shows a soft-sided inflatable embodiment. Such cells may be air-driven, pneumatic, or electro-mechanical, or may use other known means for actuation. Both embodiments include a sensor 124, and may additionally include a variable tactile sensation element 122, electrically connected to and controllable by the controller, for varying the tactile feel of the mattress top. In this respect, the tactile sensation can be selected to provide a spongy, granite-like, or pillowtop-like sensation.

Each of the support cells, 120, or the frame 110 of the bed may also contain additional sensors including but not limited to: patches, infrared sensors, sonar sensors (to determine if there is a bone near the bed surface), other sensors, camera, geographic positioning system (to detect location of patches worn on the sleeper's body to sense the relative position of the sleeper's body), sensors capable of taking measurements of periods of REM sleep, and so forth. Such sensors may also be connected to the controller, 200, through the communications cabling, 220, or some other means of communicating with the controller, for example, a wireless, e.g., Bluetooth, connection. Software on the controller, 200, may use the additional data to provide an even more detailed data set describing position of a person who is recumbent or otherwise resting upon the support system, 100. The controller may use triangulation of sleeper attached sensors which emit signals or provide an interactive response to stimuli to actively track sleeper position.

Alternatively or additionally, one or more external sensors, 202, 203, such as one or more visible spectrum cameras, millimeter wave cameras, infrared cameras, can be used to determine position and/or reposition. The controller may use triangulation of such external sensors to actively track sleeper position.

The body position information measured by the support cells, 120, is communicated to the controller, 200, through the communications cabling, 220, which may comprise separate wires for communication of the body position information sent from the cells to the controller and commands sent from the controller to the cells. Software resident on the controller, 200, may collect and interpret the data provided by the support cells, 120, on a real-time basis, and determine the location of all body parts of a person who is recumbent or otherwise resting on the support system, 100. The controller, 200, may be further programmed to increase or decrease the firmness of individual support cells within the support cell array in response to sleeper/user body position data received from the support cells, as described more fully below.

Such sensors may also be connected to the controller, 200, through the communications cabling, 220, or some other means of communicating with the controller, for example, a wireless, e.g., Bluetooth, connection. Software on the controller, 200, may use the additional data to provide an even more detailed data set describing position of a person who is recumbent or otherwise resting upon the support system, 100. The controller may use triangulation of sleeper attached sensors which emit signals or provide an interactive response to stimuli to actively track sleeper position.

In alternative embodiments, the support cells, 120, may be filled with varying amounts of air or some other gas, may be filled with varying amounts of water or some other fluid, or any other suitable matter. Alternately, the support cells can be constructed of springs with an optional top layer of cushioning, for example 8 way tied springs with a pillow top. The support cells may form any shape, for example, they may be cylindrical in shape, as shown in FIG. 1, or may be other combinations of suitable shapes, for example, spheres, cubes, or polygonal solids.

Each of the support cells, 120, is independently capable of increasing or decreasing in height from a common plane, firmness or pressure, tactile sensation (does the top feel squishy, like granite, like a pillowtop, etc—could have separate pneumatic system on top of the cell to control this), springiness, amount of hysteresis, dampening, range of motion (over what range is it springy), or size in response to commands issued by software on the controller, 200, to the support cells, 120, through the communications cabling, 210. For example, fluid or gas filled cells could be caused to inflate or deflate on command. Optionally, support cells incorporating fluid or gaseous materials could also increase or decrease in temperature in response to commands issued by software on the controller, 200, to the support cells, 120, through the communications cabling, 210. The system can optionally provide heating or cooling to the user/sleeper's body from various temperature control systems including but not limited to radiant, hydronic, forced air, etc.

The communications cabling 210 between the support cells 120 and the controller 200 may be any kind of standard communications interface suitable for linking the support cells to a computer/controller, for example, serial, USB, or Ethernet cabling and interfaces. Alternatively, the cabling, 210, could be replaced by wireless connections.

The controller, 200, has one or more software programs resident on the controller which are capable of analyzing data received from sensors on support cells, 120, sensors on the bed frame, and sensors external to the system. The controller, 200, also has one or more software programs resident on the controller which are capable of controlling support cells, 120, and any other devices, for example, heating or cooling devices, incorporated within the support system, 100. Optionally, the controller, 200, may be connected to an external network, 300, for example an IP network providing Internet access, enabling the controller to exchange data with external systems and receive programming updates.

Optionally, the controller, 200, may also host one or more databases containing data from physicians or other sources regarding, for example, anatomical data, and data collected by the system during use. Such data may be included in the database delivered with the system and/or data can be added after the onset of the use of the bed via internet or wireless or download via any other means including but not limited to compact disc or DVD or other means of storing data for download.

The additional data may, for example, contribute data regarding the anatomy of human which may, for example, be used, in conjunction with the data gathered by the sensors which may be part of the digital bed and which sensors may gather various data regarding the physical position of the sleeper's body on the digital bed, to predict whether the sleeper's spine is in the position which is intended and/or which is prescribed by physicians or others.

Optionally, the controller may also have a Graphical User Interface (GUI) on a display device, 230, with which to input data to the controller, 200, and control controller operation. If such a GUI and display device are present, the controller, 200, may also be used as a Personal Computer. The display device may be a PC, terminal, or television set.

Optionally, the system may also include devices to provide music or audiovisual programs at the direction of software resident on the controller, 200. Devices may also be included to enable selective massage therapy or vibrations targeted to specific portions of the body via, for example, vibrating transducers or rollers at the direction of software resident on the controller, 200. Heart rate measurements can be calculated based upon pressure sensor feedback, and such measurements can be utilized by software in connection with controlling such transducers. Additional devices providing other sensory input, such as light, scent, aromatherapy, various tactical stimuli, and various lights stimuli.

The system may further provide television settings before and during sleep onset and during the sleep experience. The system may further provide auditory reading of text before and during sleep onset and during the sleep experience. Simultaneously, the system may collect various data during the users' time while using the system analyzes the statistical data to determine the settings that will increase the likelihood of high quality of sleep for each particular user along various criteria.

Embodiments of the system can be programmed to provide differing amounts of pressure to support each different part of the body in a different manner. Such programs have many potential applications. For example, people who have physical pain may find it difficult to sleep. One of the reasons that people in physical pain may have difficulty sleeping is that they may have difficulty finding a comfortable position which facilitates sleep. A variety of physical pains may be alleviated or ameliorated during sleep by this invention and thereby such individuals who are constantly experiencing physical pain may find increased comfort which allows increased duration of sleep.

In one such example, an obstetrician may choose to recommend that a pregnant woman sleep on her stomach. The obstetrician might simultaneously prescribe a setting for the Digital Bed System which allows the pregnant to sleep on her stomach and simultaneously: (a) the system may provide a large recession below the woman's stomach, and (b) provides support to maintain a good relatively straight spine position. The Digital Bed System accomplishes this particular sleeping (or resting) solution for the pregnant woman by causing the bed to be very firm at particular weight bearing locations where there is bone. With this solution, the Digital Bed System provides the pregnant woman with an extremely comfortable sleeping (or resting) position.

More specifically, the pregnant woman may find that the following bones are able to comfortably support her body while she is sleeping on her stomach: the point of her hips; the bottom bones of the rib cage; the clavicle bones; the thigh bones, the shin bones. The system can automatically sense where these hard tissues (bones) are located on the bed no matter which direction the pregnant woman may be laying on the bed. The system can automatically increase pressure on these particular hard tissues (bones) and decrease pressure at all of the appropriate points of the body.

In another such example, a person with excess weight can be aided by the by keeping the person's spine in a straight position. The system may accomplish this by lowering the pressure under the stomach when the person is sleeping on his/her stomach or by increasing the pressure under the lower back when the person is sleeping on his/her back. The goal is to keep the spine in a natural position which may be near a straight position with some customized curves depending on the individual's natural spine shape. Similarly, Individuals with Scoliosis can be aided immensely by relieving the pressure on their spine while they sleep.

The system may be configured such that, if any one cell malfunctions, the controller 200 causes its neighboring cells to assume the functions of the malfunctioning cell. In systems wherein fluid filled cells are utilized, the malfunctioning cell can be caused to deflate.

The system may enable a particular sleeping (or resting) solution for the pregnant woman by causing the bed to be very firm at particular weight bearing locations where there is bone. With this solution, the system provides the pregnant woman with an extremely comfortable sleeping (or resting) position. In particular, the pregnant woman may find that the following bones are able to comfortably support her body while she is sleeping on her stomach: the point of her hips, the bottom bones of the rib cage, the clavicle bones, the thigh bones, and the shin bones.

The system may automatically sense where these hard tissues (bones) are located on the bed no matter which direction the pregnant woman may be laying on the bed. The system can automatically increase pressure on these particular hard tissues (bones) and decrease pressure at all of the appropriate points of the body.

The system may also provide the capability for a sleeping person to maintain one or more prescribed positions of the spine throughout a night's sleep even when the person may roll over and changes positions many times throughout the night. For example, a particular person may prefer to maintain a particular spine position(s) during sleep even while the sleeper changes positions throughout the night's sleep. In general, the system may additionally assists the bodily comfort of a sleeping person by keeping pressure off of a person's belly, breasts, hips and ribs, thigh bones, knee caps, and/or the instep of the foot (the location that is sometimes covered with shoelaces.)

In another example, some people may sleep on their stomachs with their feet hanging off of the end of the bed in order to allow their legs to be in a straight alignment from the hips all the way to the ankles. In other words, when sleeping on their stomachs, some people find that if they keep their feet on the bed, then their toes are pressed uncomfortably into the mattress and their heels are unnaturally propped upwards into the air. Thus, the legs are bent at the knees, and the knee caps are pressed into the mattress.

The system can allow this particular type of sleeper to keep their feet and toes on the bed. The system may allow for a recession (or lowering of pressure) in the support cells, 120, located underneath the person's toes and instep. Thus, the person can sleep on her or his stomach without hanging their toes off of the end of the bed, and simultaneously the persons legs can be in a position that is ergonomic (relatively straight) from hips all the way to the ankles. When lying face down, the toes can be well below the general surface level of the digital bed. Addtionally, the system may allow for a recession to pressure off of shoelaces so the feet can virtually (perceptively) "hang off of bed."

In another example, the knee caps can be located by sensors which detect a protrusion pressing into particular cells, and then the system can automatically cause the cells under the knee caps to soften and/or deflate in order to relieve pressure off of the knee caps. The system may also apply higher pressure at all bone support points of the body such as shoulders and hips and length of thigh and shin bones.

The system may allow the sleeper's arms to hang straight down toward the floor via the computer altering the contours of the digital bed, and the contours surrounding the arms can be altered by the computer to protect the sleeper's arms from being hurt in the event the sleeper's body rolls over. In the event that a sleeper/user hangs their arm down underneath the sleeper's/user's body and simultaneously there is bed material between the sleeper's body and the sleeper's hand, then the digital bed can provide support for the sleeper's body weight directly above the location of the sleeper's hand by horizontal support of the digital bed (to replace the direct vertical support which is interrupted by the position of the sleeper's hand). Thus, the sleeper on the digital bed can hang their arms downwards and inwards toward the center of the sleeper's body and meanwhile the sleeper's body will still be fully supported. Thus, the sleeper can have the sensation of "hugging" the digital bed as if parts of the digital bed turned into a big pillow to be "hugged."

The system may use (1) statistical data on the digital bed's hard drive and/or (2) the data gathered by sensors and/or (3) the various prescribed positions for the physical body of the user of the digital bed or the sleeper on system in order to determine the optimum position of the digital bed for the particular user's skeletal muscular positions for the user's body while resting or sleeping. For example, if the user's physician prescribes that a sleeper's spine be kept as straight as possible, then the system can adjust for varying body shapes of various sleepers and the system can determine the likely location of each sleeper's vertebra (spine) even though various users' bodies have different shapes.

The system may also use GPS or sensors to detect location of patches worn on the sleeper's body to sense the relative position of the sleeper's body and the relative position of the sleeper's spine. The patches are placed strategically on the sleeper's body. Through the use of these patches, the spine can be kept in horizontally straight position. The system be programmed to adjust automatically every time the sleeper moves so that the pressure inside of the support cells dynamically changes to return the spine to a horizontally straight position.

A person knowledgeable in the art can understand that there are other methods to gather the information on the shape of the individual sleeper's body and the position of the body in the Digital Bed and the interpolation of data to determine the position of the spine and the skeletal muscular system of the sleeper(s).

Specialized custom settings and/or customization of computer programs resident on the controller, 200, may also be made to customize the bed's support system to account for injuries such as, for example an injured, sensitive knee cap. The system can be programmed to reduce the pressure on that knee cap and the bed's computer program can accomplish that function even with the dynamically changing sleeping positions that may occur throughout the night' sleep. In another example, a broken leg could be immobilized by the system, and the system could dynamically maintain immobility of the leg even if the person changes sleeping positions.

The system could be additionally programmed to cause an injured joint to be surrounded by either cold or warm water. The system may also be programmed to provide a slight stretching exercise of different muscles in the body by causing a camber shape (for example) to appear under the particular area of the body which needs to be stretched. Similarly, the system may be used for traction as prescribed by a physician, which may include allow a sleeper to sleep in a variety of positions, such as vertically or at any angle Employment of additional sensors or measuring devices may allow the treatment of more complicated conditions. For example, monitors may be employed within the system to gather information pertaining to quality and duration of sleep, including but not limited to: brain wave scans, magnetic resonance imaging, measurement devices which monitor levels of various chemicals and gases in the body, and sleep apnea measurement devices, etc. Such data would be communicated to the controller, 200, to allow the controller to take appropriate action to enhance the quality of a person's sleep.

For example, the system may gather data on, without limitation, the speed of onset of sleep, maximum REM sleep (by, for example, using sensors to constantly obtain data on the user's eyes), the length of REM sleep, the number of REM sleep episodes, the amount of time needed to begin first REM sleep episode, the number of total hours of sleep, the number of occurrences of rolling around, the number of occurrences of waking up in the middle of the night, etc. Such data may be compiled over many nights of an individual's sleep and correlated to all conditions and settings of the system. The system may then use this information in order to make slight adjustments to the system to maximize REM sleep, minimize sleep disruptions (tossing and turning) and increase comfort and therapeutic body support during the sleeping hours. The system may be also set to wake up the sleeper after the sleeper has slept for a certain amount of time or optionally after the sleeper has experienced a certain amount of REM sleep or optionally based on other criteria chosen by the computer or the user.

Besides the data gathered during the users sleeping episodes, the user can also provide self report data after each sleeping episode for input into the system and which can be used by the system to correlate the optimum settings to maximize the likelihood of the highest quality sleep for the user of the system during future sleeping episodes. Note also, that if the system is connected to the Internet, a users sleeping patterns may be monitored remotely by, for example, a physician. Furthermore, the system may also utilize statistical information from the data gathered from other sleepers and use this information to suggest digital bed settings to increase speed of onset of sleep.

The system may be programmed to create profiles stored on the controller which may be used to identify different users by, without limitation, body shape and/or by the user inputting their name or otherwise identifying themselves. Such profiles enable the system the to issue commands to change the position of individual support cells within the array of support cells in accordance with the profile, enabling the system perform, without limitation, one or more of the functions described in this disclosure for a specific user. The profile may be created in accordance with user preferences input to the system, for example, through the system's GUI, or alternatively, from a source external to the system, such as a network connected to the system. Alternatively, the profile may be created using a combination of statistical analysis of other users of the system and the user's preferences. The system may additionally include a reader for reading the profile from a portable digital storage device. The system may be further configured to receive a user's profile from a network connected to the system, for example, the internet. Doctor-prescribed profiles may be stored in the system for addressing, e.g., chiropractic and other ailments.

The system may be further configured to allow two simultaneous users, each with their own profile. For example, a husband and wife can utilize the Digital Bed simultaneously and each of the spouses would be receiving their own interaction with the system. Thus, two people would be able to sleep together on system. The system may perform, without limitation, one or more of the functions identified in this disclosure separately for each person. The settings of the system would also take into account if the couple was sleeping in the "spoon" position, for example. The system would maximize the quality of sleep for the two users. The system could be configured such that any user could port their customized settings to any digital bed system.

The system may raise certain areas of the bed to provide increased support under the head, for example, to decrease the need for use of a pillow. When the sleeper is sleeping on her back, the digital bed may optionally provide support for the sleeper's head with lateral supports which keep the sleeper's head from tilting to either side.

Other uses for the system are also possible. For example, the system may also be used as an alarm clock. When set to wake up a sleeping person the system can wake the person by causing slowly ascending waving action or slowly ascending rumbling action or audio or lights or other stimuli such as music, television, etc.

The system may also be programmed to create special effects to encourage relaxation. For example, the system could spin and create a centrifugal force on the user's body; alternately the system could create a feeling of swaying in the wind or weightlessness. Other stimuli (including but not limited to colored lights, scents, sensations, other stimuli, etc) of all types may be provided during different stages of wake and sleep in order to add the best benefits to the user's experience of using the digital bed. The system may also provide slow and small movement which may be imperceptible to the sleeper but which may augment the sleep experience by alleviating stagnant pressure over the hours of sleep and which may lessen the need for the sleeper to change positions during the course of the night. Alternatively, the system may also provide undulating message or other vigorous massages for one or two people to enjoy simultaneously.

The digital bed can also obtain data related to improving the sleep experience, for example data pertaining to encouraging REM sleep, from the internet.

The system may provide the capability to drain any fluids as needed, and may be provided with the capability to predict the need to drain fluids in order to minimize the likelihood of fluids contacting the sheets or contacting the bed surface. The digital bed system can have the capability of sanitizing the bed as needed. The Digital Bed can have the capability of efficiently minimizing the inconvenience of a child who has a bed wetting issue. Furthermore, system may have the capability to use sensors to detect when there is any insect of bed bug or other undesirable item on the Digital Bed and the capability to efficiently eradicate that undesirable item with maximum sanitizing effect on the bed and the bed coverings.

The system may have a refrigerator and/or a heat source (for hot beverages) built in to the Bed or associated with the bed and liquid refreshment may be delivered by the system as part of the waking up experience whereby the user can set a time be awaken and then the user can choose between various stimuli to be used to wake up the user and cold or hot beverages may be served up by the system via a tube or via automatically filling a cup or glass. Similarly, food can be delivered to the user of the system. The system can provide beverages to the user and predict the likelihood that the user may be thirst based on data collected from sensors that is correlated to thirst.

A person knowledgeable in the art can understand that there are various methods to accomplish this type of body support possibly for sleeping while seeming to "float," as it were. The floating sensation can alternately be accomplished by magnets supporting the sleeper's body weight without touching the sleeper's body. The magnets would be "levitating" (as it were) the sleeper's body because the sleeper has attached pieces of metal (for example) to his/her body which interact with the magnets and cause the sleeper's body to "float" or "elevate" or "levitate" (as it were).

The system can have the capability to create any shapes of parts thereof that provide tactile stimuli.

Another method of supporting the sleeper could be to utilize metal wires (or other material) suspended from above (and/or below) which support pads placed under the sleeper's body. Each pad (or other material) functions as a support cell which can be controlled by the system in order to create the most ergonomic sleeping position whereby the REM sleep is maximized, the tossing and turning is minimized, the spine is in a selected or prescribed position, and/or the spine is in a natural position with natural curves customized for each individual sleeper.

The system may also optionally also include a material which, for example, can be placed on top of the user's body in order to create a pressure from above and/or a pressure from the sides. This allows compression of the user's body or parts of the body. This allows for massage and other uses including but not limited palliative or medical uses. If the support system covers all sides of a person's limb or all sides of a person's body, a person could sleep in a suspended state, totally surrounded by water on all sides.

The system may also be implemented as an easily transportable pad which may be used anywhere, or as an entire room which functions as a support system.

In other embodiments, the Digital Bed may be constructed such that when support cells change in size or shape, alone or in combination, the overall form of the Digital Bed changes, and may assume the form of a different piece of furniture. Such furniture may be referred to generally as Digital Metamorphosis Furniture.

One embodiment of Digital Metamorphosis Furniture is a Digital Bed which can undergo a user controlled metamorphosis resulting in the Digital Bed becoming (or morphing into or changing into the physical shape of) any number of other items of Furniture or Decoration including but not limited to metamorphosizing (hereinafter "morphing") into a lounge chair, a desk, a combination of desk and chair, a piece of wall art, a combination of two chairs and a breakfast table, a table to support a television, a bed with adjacent nightstands, etc.

For example, the user may be able to choose or to cause the Digital Bed to morph into a Lounge Chair. As a result of this choice by the user, the various cells of Digital Bed would be partially "deflated" and/or partially "inflated" so that the Digital Bed becomes the shape of a Lounge Chair, for example. The user could choose among various shapes and types of chairs or various other pieces of furniture or various objects. For example, the user could select to morph the bed into a specific user selection of a particular club chair, for example, which is particularly suited for the user's body height, shape, weight, and comfort. As a result of a user's particular selection, the Digital Bed would morph into a Digital Chair which would be customized to provide the maximum comfort for that particular user's body.

The computer or controller which controls the settings on the Digital Bed and which controls the morphing into an optional Desk and Desk Chair may also have a monitor with a Graphical User Interface. The combination of the computer or controller (which controls the setting on the various pieces of digital furniture and which controls the morphing functionality) and optional monitor can be used as a personal computer which can optionally be located on top of the Digital Desk (which was optionally morphed from the Digital Bed).

Where electrical sensors are provided in the system, such sensors can be utilized to monitor heart and brain functions via EKG, alpha and beta brainwave measurements. Data taken can be utilized to generate reports, compare measurements to a baseline for an individual sleeper, and other medical analyses. Such data or reports can be transmitted to medical personnel, or can be used to trigger an alarm state that causes notification of medical personnel, including emergency response personnel. The system itself may, upon triggering of a particular alarm, be caused to apply or begin treatment, such as by cooling the body in the case of a stroke, or defibrillation in the case of a cardiac event.

The system may include a means for analyzing audio or vibrations to detect snoring. In response to such detection, the system may apply a program to the cells to encourage repositioning of the body or otherwise lessen the likelihood of continued snoring or increase the likelihood clear breathing or other desired physiological response.

The monitor and/or computer can optionally be provided to be used by the user as Television. The user can choose the location that the Television will be mounted on the Desk or on the Digital Bed or other object, as selected by the user. Thus, the user can choose to set the settings via the computer to cause the Digital Desk to morph back into the Digital Bed with the Television optionally mounted near the foot of the Digital Bed.

The result is that the user can choose to watch television shows on the television (which television is optionally included as part of the apparatus) while lying on the Digital Bed. Alternately, the user can select to watch television shows while the user is sitting at the Digital Desk Chair (for example after the Digital Bed is morphed into the Desk and Desk Chair) with the television mounted on the Digital Desk.

The support cells within the system may be colored to increase the aesthetic appear of any furniture or art formed by the system. Alternatively, the color of the cells may be variable or be backlit, and change on command.

While the invention has been particularly shown and described with reference to embodiments discussed above, it will be understood by those skilled in the art that various changes in form and details may be made therein without departing from the spirit and scope of the invention. For example, without limitation, the system can have various decorative colors and materials. The computer can control the color and the materials to provide the user's preference for aesthetic appearance.

What is claimed is:

1. A digital bed system that actively monitors and dynamically adjusts its sleeping surface, the digital bed system comprising:
    a bed having an array of at least four independently controlled support cells, each of the support cells being configured to communicate with a controller, each of the support cells comprising an actuator configured to change position in response to commands issued by the controller so as to reshape a sleeping surface of the bed, the reshaping of the sleeping surface of the bed resulting from a change in at least one of the actuators;
    a communication channel operatively connecting each of the support cells to the controller;
    a plurality of sensors operatively connected to the controller and configured to gather measurements relating to a state of at least one user's body or part thereof and to output signals comprising data reflecting the measurements relating to the state of the at least one user's body or part thereof;
    the controller being configured to receive the signals comprising data from the plurality of sensors, the controller being further configured to send a command signal comprising commands to each of the support cells, the controller being further configured to use the data received from the plurality of sensors to determine a position of the at least one user's body or part thereof and use the position to determine a change of position of a plurality of support cells within the array of support cells, the change of position being one that places the at least one user's body or part thereof in a selected position, and to send a signal comprising commands to at least one of the plurality of support cells to dynamically change position of the at least one of the plurality of support cells to place the at least one user's body or part thereof in the selected position;
    wherein the controller is programmed to actively monitor the position of the at least one user's body or part thereof laying upon the sleeping surface and programmed to dynamically issue commands to the plurality of support cells within the array of support cells, over the communication channel, to change the position of the plurality of support cells within the array of support cells in response to a determination by the controller that the at least one user's body or a particular part thereof is in a particular position, the particular position being among at least two positions programmed into the controller and specifically detectable by the controller.

2. The digital bed system in accordance with claim 1, wherein the plurality of support cells, in response to the commands, change in at least one manner selected from the set consisting of: height from a common plane, firmness, pressure, springiness, amount of hysteresis, dampening, and range of motion.

3. The digital bed system in accordance with claim 1, wherein the plurality of support cells, in response to the commands, change in tactile sensation in at least one manner.

4. The digital bed system of claim 1, wherein at least one of the support cells is capable of sensing and communicating pressure data to the controller and wherein the controller is programmed to accept body position data from the support cells, the controller being further programmed to increase or decrease firmness of individual support cells within the array of support cells in response to the body position data received from the support cells.

5. The digital bed system of claim 1, wherein at least one sensor of the plurality of sensors is integrated with a support cell of the plurality of support cells.

6. A digital bed system that actively monitors and adjusts its sleeping surface, comprising:
    a two-dimensional array of support cells in communication with a controller, each of the support cells comprising an actuator configured to change position in response to commands from the controller so as to reshape a sleeping surface of a bed, the reshaping of the sleeping surface of the bed resulting from a change in at least one of the actuators;
    a plurality of sensors configured to gather measurements relating to a state of a sleeper or part thereof and to output signals comprising data reflecting the measurements;
    a communication channel operatively connecting the controller to each of the support cells and the plurality of sensors;
    wherein the controller is configured to receive the signals from the plurality of sensors and programmed to send a first command signal to the array of support cells to change the position of one or more of the support cells, the controller being further configured to determine a likely position of the sleeper or part thereof and use the likely position to determine a change of position of a plurality of the support cells within the array of support cells to place the sleeper or part thereof in a selected position, and to send a second command signal to dynamically change position of the plurality of the support cells to place the sleeper or part thereof in a selected position;

wherein the controller is programmed to actively monitor the array of support cells and to dynamically issue commands to the plurality of support cells within the array of support cells, over the communication channel in real time to increase or decrease the size of, or change the shape of, the plurality of support cells within the array of support cells in response to a determination by the controller that the sleeper has changed position, the determination being either that the sleeper has rolled over or that the sleeper has changed from a first body position programmed into the controller to a second body position programmed into the controller, the first and second body positions being detectable by the controller.

7. The digital bed system of claim 6, wherein the controller is programmed to issue commands to increase or decrease the size of, or change the shape of, a combination of one or more individual support cells within the support cells wherein the digital bed assumes a second shape.

8. The digital bed system of claim 7, wherein the second shape is one of the following: a chair, a table, or a bed with adjacent nightstands.

9. A digital bed system that actively monitors sleep conditions of a particular sleeper and adjusts a sleeping surface, comprising:
an array of at least four independently controllable support cells, each of the cells being configured to communicate with a controller, each of the cells comprising an actuator configured to change position in response to commands issued by the controller;
a communication channel operatively connected to each of the cells;
the controller operatively connected to the communication channel, the controller being configured to receive a signal over the communication channel and to use the signal to determine a likely location of the sleeper or part thereof, and configured to use the likely location to determine a change of position of at least one of the support cells within the array of support cells, the change of position being one that places the sleeper or part thereof in a selected or prescribed position, and to send a signal over the communication channel, the signal comprising commands to at least one of the support cells that dynamically change position of at least one of the support cells to place the sleeper or part thereof in the selected or prescribed position, such that an ergonomic sleeping position results, the controller being programmed to issue send a signal comprising commands to at least one of the support cells in response to a change in the sleep conditions;
wherein, the controller is programmed to store a profile, and to send a signal comprising commands to at least one of the support cells within the array of support cells, over the communication channel, to change the position of the at least one of the support cells within the array of support cells so as to reshape the bed in accordance with the profile, the reshaping of the bed resulting from a change in at least one of the actuators; the profile being associated with the particular sleeper and including instructions as to how to change the position of the individual support cells in response to at least one change in the sleep conditions, the controller being programmable with at least one individual profile associated with at least one user.

10. The digital bed system according to claim 9, wherein the controller includes a network interface for receiving the profile via a connected network.

11. The digital bed system according to claim 9, wherein the profile is created in accordance with the user's preferences.

12. The digital bed system according to claim 9, wherein the profile is created using a statistical analysis of other users and in accordance with the user's preferences.

13. The digital bed system of claim 9, wherein the controller is further capable of determining a specific location on the bed where the sleeper's bones protrude into the bed and a specific location on the bed where soft tissue is being pressed by the bed.

* * * * *